United States Patent

Mast

[11] 4,078,858
[45] Mar. 14, 1978

[54] MEASURING HEAD
[75] Inventor: Fred Mast, Wil, Switzerland
[73] Assignee: Gretag Aktiengesellschaft, Regensdorf, Switzerland
[21] Appl. No.: 754,222
[22] Filed: Dec. 27, 1976
[30] Foreign Application Priority Data
Dec. 30, 1975 Switzerland ............ 16872/75
[51] Int. Cl.² ............................................ G01N 21/48
[52] U.S. Cl. ................................................. 356/210
[58] Field of Search .................. 356/209, 210, 211; 250/574

[56] References Cited
U.S. PATENT DOCUMENTS

| | | | |
|---|---|---|---|
| 3,246,561 | 4/1966 | Sweet | 356/209 |
| 3,774,039 | 11/1973 | Price | 356/211 |
| 3,996,476 | 12/1976 | Lazzara | 250/574 |

Primary Examiner—John K. Corbin
Assistant Examiner—R. A. Rosenberger
Attorney, Agent, or Firm—Burns, Doane, Swecker & Mathis

[57] ABSTRACT

A head for measuring light diffusely reflected from a surface, the head having an optical projection system for projecting light onto a surface to be measured, and another optical system for collecting the light diffusely reflected from that surface and imaging it on a photodiode. The collecting optics comprise a spherical annular mirror coaxially aligned with an annular transparent planar member which has an annular plane mirror mounted underneath it, the projected light passing through the apertures in the annular mirror, the planar member, and the annular planar mirror. The light diffusely reflected from the surface to be measured passes through the planar member onto the spherical mirror which reflects it back through the member onto the planar mirror which in turn reflects it back through the planar member onto reducing optics which images the reflected light onto the photo-diode.

11 Claims, 1 Drawing Figure

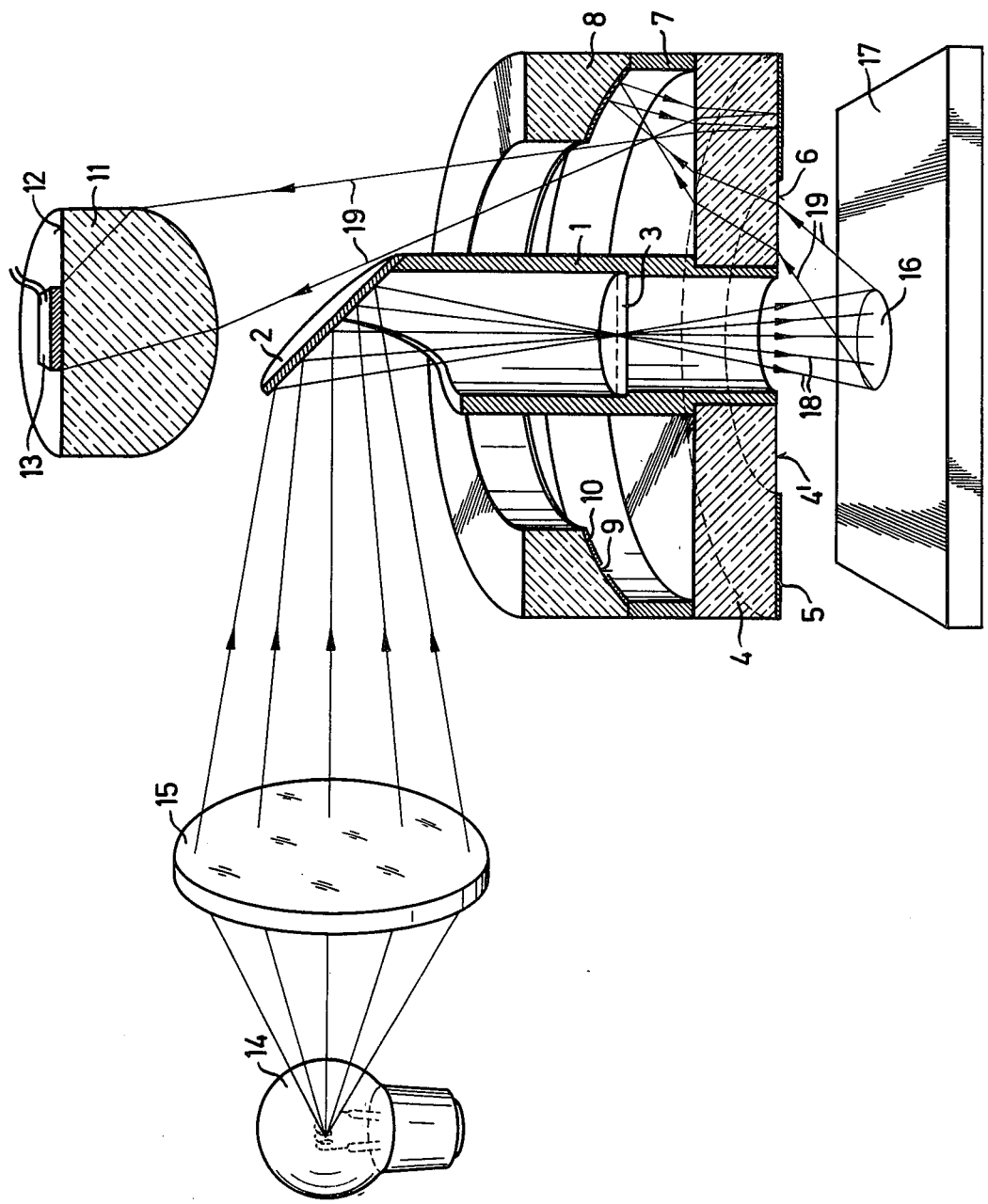

MEASURING HEAD

FIELD OF THE INVENTION

The invention relates to a measuring head for determining the optical diffuse reflection properties of an object.

Determinations of the optical reflected diffusion properties of surfaces can of course provide predictable results only when carried out to specific standards. US Standard PH 2.17-1958 is one such standard. One of its requirements is that the object or target should be illuminated by a beam having an angular size of 10° and incident normal to the target surface and that only the light which is diffusely reflected over an angle of 45° ± 5° to the input slot shouldbe examined. Reversibility is permitted but has a less favourable energy balance and is therefore less suitable, more particularly in cases where only relatively weak light sources are available.

PRIOR ART

In one known measuring head comprising projection optics for illuminating the measured object or target and collecting optics having a silvered ring for the light diffusely reflected by the target at a predetermined angle to the optical axis of the projection optics the ring takes the form of a simple conical silvered mirror which projects light diffusely reflected by the target on the entry aperture of a photomultiplier. Unfortunately conical mirrors suffer from spherical aberration, with the result that the usually very small spot of the target cannot be imaged on a comparably small surface. In practice therefore it is necessary to use photomultipliers for photoelectric measurement of the diffusely reflected light, for only photomultipliers have a large enough light entry aperture or a large enough light-sensitive surface plus adequate sensitivity but they are expensive.

Apart from some special purposes, photomultipliers are being used less and less; their places being taken more and more by semiconductor photoelectric converters such as silicon planar diodes, because of their cheapness and because they are simple and easy to use. However, since large size semiconductor elements are more costly, they have not yet been used, despite their great advantages, for diffuse reflection measuring heads, at least for the kind having the beam path defined above. Of course a collecting optics systems able to cope satisfactorily with the smallness of such semiconductor elements could be devised, e.g. by means of complicated ellipsoid mirrors and/or lens systems comprising a number of lens elements, but they would be very elaborate and would reduce the cost advantage of semiconductor elements over photomultipliers.

BRIEF SUMMARY OF THE INVENTION

It is therefore an object of the invention to improve the measuring head referred to above so that it can use small photo semiconductors to evaluate the diffusely reflected light.

The head according to the invention therefore employs a silvered ring which is spherical, a transparent plate disposed in the path of the beam in the collecting optics before the silvered ring, and a substantially plane silvered ring mirror and reducing optics disposed in such path after the spherical silvered mirror.

DETAILED DESCRIPTION OF PREFERRED EMBODIMENT

A preferred embodiment of the invention will be described in greater detail hereinafter with reference to the accompanying drawing, which is a longitudinal section through a measuring head according to the invention; merely those parts which are important to the invention being shown.

The main element of the complete system is a light tunnel or shaft 1 which is open at both its ends and which has a plane reflecting mirror 2 at its top end. A collecting lens 3 is disposed approximately at the centre of the shaft or tunnel 1. Disposed at the bottom end thereof is an annular plane parallel glass plate 4 having an annular mirror 5 vapour-coated to its underside 4'. The mirror 5 does not cover the complete under-surface of plate 4 but leaves an annular light-transmitting window 6 free.

An annular glass member 8 is mounted above the plate 4 by a spacing ring 7, and has on its underside a spherically curved concave annular surface 9 having vapour-coated thereon a ring mirror 10.

Above mirror 2 is an aplanate or rapid rectilinear lens 11 having a plane light exit surface 12 to which is secured a photoelectric converter in the form of a silicon planar diode 13.

Light emitted by a light source 14 and passing through a lens 15 to impinge on reflecting mirror 2 is reflected thereby into the shaft or tunnel 1 and concentrated by collecting lens 3 on to a measurement spot or target 16, of e.g. approximately 3 mm diameter, on a surface 17 whose diffuse reflection is required to be measured. As specified in the aforementioned U.S. Standard, the light beams 18 are incident on surface 17 at angles in the region of from 85° to 90°. Some of the light reflected diffusely by the target 16 passes through the window 6, the glass plate 4, and impinges on the spherical ring mirror or silvered ring 10, where it is reflected back through the glass plate 4 onto mirror 5 and back again through the glass plate 4 onto the aplanate 11 which projects it on the photodiode 13. The geometry of the complete system is such that the photodiode receives only light which has been diffusely reflected at angles of approximately 45° ± 5° to the surface 17.

The optics for collecting the diffusely reflected light comprises four parts — the plane parallel glass plate 4, the spherical ring mirror 10, the plane ring mirror 5 and the aplanate 11 — and all these items can be produced fairly simply and cheaply. The main function of the plate 4 is to remove the spherical aberration caused by the mirror 10. The plate 4 if made of ordinary glass having a refraction index of approximately 1.55 has a thickness of approximately 0.15 to 0.25 times the radius of curvature of the spherical mirror 10. Another feature which has been found to be convenient in practice is for the system to be designed so that the magnification provided by the elements 4, 10, and 5 is approximately 3 or less. This feature is directly related to the aplanate 11, since the maximum reduction which the same can provide is somewhere in the region of 3, depending upon the glass quality. Of course, the above features only relate to those cases in which the active surface of the photodiode is of approximately the same size as the illuminated area of the target. The magnification requirements are less important for relatively large photodiodes. However, since photodiodes of more than 3 mm diameter are more costly and since there are virtually no photodiodes commercially available with diameters of more than 6 mm, there are limits to the size of photodiodes which can be used.

An appropriate lens system could be used instead of the aplanate 11 and the photodiode 13 could be located at a distance from the aplanate instead of directly thereon. Nor need the glass plate 4 be plane and parallel; for instance, it could be in the form of a spherical shell. In this event, however, the shell radii should be not less than approximately 3 times the radius of curvature of the spherical ring mirror. The main factor — applies to all the parts of the measuring head — is easy and simple manufacture. It is not essential for the mirrors 10, 5 to be formed as vapour coatings on glass substrates. It is convenient for the plane mirror to be in optical contact with the plate 4 only if disposed on the underside thereof. Nor is the latter feature essential, but it helps to reduce the overall size of the complete measuring head. Any appropriate plastics can be used instead of glass for the various transparent items.

What is claimed is:

1. A head for measuring the diffuse reflectivity of an area of a surface, said head comprising;
    a first optical system projecting a beam of light onto a predetermined area of a surface whose diffuse reflectivity is to be measured,
    a transparent member mounted to transmit light diffusely reflected from said surface,
    a plane mirror,
    a spherical mirror mounted to reflect light transmitted by said member onto said plane mirror, and
    a second optical system for imaging the light reflected from said plane mirror.

2. A head according to claim 1, wherein the member is a plane parallel transparent plate having a thickness approximately 0.15 to 0.25 times the radius of curvature of the spherical mirror.

3. A head according to claim 2, wherein the plane mirror comprises a coating on one surface of the plate, remote from the surface facing the spherical mirror.

4. A head according to claim 2 wherein the enlargement provided by the plate, the spherical mirror and the plane mirror is at most approximately 3 : 1.

5. A head according to claim 1 wherein the second optical system comprises a rapid rectilinear lens.

6. A head according to claim 2 including an annular glass member and an annular spacing ring interposed between said plate and the annular glass member, said spherical comprising a reflective coating on one surface of said annular glass member.

7. A head for measuring the diffuse reflectivity of an area of a surface, said head comprising;
    a light source,
    a first plane light reflective surface,
    a first optical system projecting light from said source onto said first plane reflective surface,
    a transparent plate having parallel surfaces and defining an aperture centrally therein,
    a plane mirror below said plate
    a second optical system projecting light reflected from said plane surface through the aperture in said plate onto an area of a surface whose diffuse reflectivity is to be measured,
    a spherical annular mirror mounted above and coaxially with said plate to receive light diffusely reflected from said surface to be measured through the transparent plate and reflect the diffusely reflected light back through said plate onto said plane mirror,
    a photo sensitive element, and
    a third optical system having a magnification less than unity and mounted to image light from said plane mirror onto said photo cell.

8. A head according to claim 7 wherein said spherical annular mirror comprises an annular member coaxial with said plate, said member having a concave spherical surface on which is deposited a coating forming said spherical mirror.

9. A head according to claim 8 including a spacing ring spacing said annular transparent member from said spherical mirror.

10. A head according to claim 9 wherein said plane mirror comprises an annular reflective coating on the under surface of said transparent annular member.

11. A head according to claim 7 wherein said photo sensitive element comprises a silicon photo diode.

* * * * *